United States Patent
Elmandjra et al.

(10) Patent No.: US 8,352,006 B1
(45) Date of Patent: Jan. 8, 2013

(54) DIAGNOSING HYPOXIA BY MONITORING CHANGES IN OXYGEN SATURATION

(75) Inventors: Mohamed Elmandjra, Pleasanton, CA (US); William O'Keefe, New Braunfels, TX (US); Jian-min Mao, Fremont, CA (US); Robin Bush, Newark, CA (US); Linda Christenson, Oakland, CA (US)

(73) Assignee: ViOptix, Inc., Fremont, CA (US)

( * ) Notice: Subject to any disclaimer, the term of this patent is extended or adjusted under 35 U.S.C. 154(b) by 1254 days.

(21) Appl. No.: 11/782,394

(22) Filed: Jul. 24, 2007

Related U.S. Application Data

(63) Continuation of application No. 10/838,142, filed on May 3, 2004, now Pat. No. 7,247,142.

(60) Provisional application No. 60/468,003, filed on May 5, 2003.

(51) Int. Cl.
*A61B 5/00* (2006.01)
(52) U.S. Cl. .................. 600/323; 600/500; 600/481
(58) Field of Classification Search .................. 600/481, 600/500, 323
See application file for complete search history.

(56) References Cited

U.S. PATENT DOCUMENTS

| | | | | |
|---|---|---|---|---|
| 5,285,784 | A * | 2/1994 | Seeker | 600/331 |
| 5,931,779 | A * | 8/1999 | Arakaki et al. | 600/310 |
| 6,587,701 | B1 * | 7/2003 | Stranc et al. | 600/310 |
| 6,587,703 | B2 * | 7/2003 | Cheng et al. | 600/310 |
| 6,863,656 | B2 | 3/2005 | Lurie | |
| 6,909,912 | B2 | 6/2005 | Melker | |
| 2002/0072661 | A1 * | 6/2002 | Wiesmann et al. | 600/328 |
| 2003/0236452 | A1 * | 12/2003 | Melker et al. | 600/323 |
| 2007/0016079 | A1 | 1/2007 | Freeman et al. | |
| 2007/0024946 | A1 | 2/2007 | Panasyuk et al. | |
| 2007/0038042 | A1 | 2/2007 | Freeman et al. | |
| 2007/0249913 | A1 | 10/2007 | Freeman et al. | |

OTHER PUBLICATIONS

Myers, DE et al., "Noninvasive Method for Measuring Local Hemoglobin Oxygen Saturation in Tissue Using Wide Gap Second Derivative Near-Infared Spectroscopy," Level1Diet, J Biomed Opt. May-Jun. 2005, accessed Mar. 25, 2008, <http://www.level1diet.com/893768_id>.

Kasel, Dustin, "Tissue Oxygen Saturation as a Non-Invasive Measurement for Cardiac Output," Nov. 18, 2007, accessed Mar. 25, 2008, <http://biomedprojects.org/home/projects/papers/tissue-oxygen-saturation-measurement-as-a-non-invasive-alternative-to-cardiac-output-1>.

Comerota, AJ et al., "Tissue (muscle) Oxygen Saturation (StO2): A New Measure of Symptomatic Lower-Extremity Arterial Disease," Jobst Vascular Center, Oct. 2003, accessed Mar. 25, 2008, <http://www.ncbi.nlm.nih.gov/pubmed/14560221?dopt=Abstract>.

Kragelj, Rudi et al., "Parameters of Postocclusive Reactive Hyperemia Measured by Near Infrared Spectroscopy in Patients with Peripheral Vascular Disease and in Healthy Volunteers," Annals of Biomedical Engineering, vol. 29, pp. 311-320 (2001).

* cited by examiner

*Primary Examiner* — Patricia Mallari
*Assistant Examiner* — Michael D'Angelo
(74) *Attorney, Agent, or Firm* — Aka Chan LLP

(57) ABSTRACT

Hypoxia is diagnosed through measurements of oxygen saturation. Some examples of hypoxia conditions that may be diagnosed include peripheral vascular disease, multiple organ dysfunction syndrome, ischemia, hypotension, and arteriosclerosis. In a specific implementation, a hypoxia condition is diagnosed based on changes in oxygen saturation in tissue. Ischemia is induced, and then measurements of changes in oxygen saturation in tissue are made. Based on changes in oxygen saturation, a diagnosis is provided of whether a patient has or does not have a hypoxia condition.

32 Claims, 12 Drawing Sheets

StO2 Recovery Rate

| PTS Result | PVD status | |
|---|---|---|
| | Positive | Negative |
| Positive | a = 10 (true positive) | b = 1 (false positive) |
| Negative | c = 0 (false negative) | d = 8 (true negative) |
| Sensitivity = a/(a+c) | 100% ± 0% | |
| Specificity = d/(b+d) | 89% ± 7% | |
| PPV = a/(a+b) | 91% ± 7% | |
| NPV = d/(c+d) | 100% ± 0% | |

*FIG. 7*

Recovery to 80%

| PTS Result | PVD status | |
|---|---|---|
| | Positive | Negative |
| Positive | a = 8 (true positive) | b = 0 (false positive) |
| Negative | c = 2 (false negative) | d = 9 (true negative) |
| Sensitivity = a/(a+c) | 80% ± 0% | |
| Specificity = d/(b+d) | 100% ± 7% | |
| PPV = a/(a+b) | 100% ± 7% | |
| NPV = d/(c+d) | 82% ± 0% | |

*FIG. 11*

DIAGNOSING HYPOXIA BY MONITORING CHANGES IN OXYGEN SATURATION

CROSS-REFERENCE TO RELATED APPLICATIONS

This patent application is a continuation of U.S. patent application Ser. No. 10/838,142, filed May 3, 2004 (now U.S. Pat. No. 7,247,142, issued Jul. 24, 2007), which claims the benefit of U.S. provisional application 60/468,003, filed May 5, 2003, which are incorporated by reference for all purposes.

BACKGROUND OF THE INVENTION

The present invention relates to methods of diagnosing peripheral vascular disease (PVD) using measured changes in oxygen saturation in tissue. More specifically, the invention relates to diagnosing peripheral vascular disease from an analysis of oxygen saturation during recovery from ischemia (reduced or stoppage of blood flow).

Peripheral vascular disease is a condition that is exemplified by a narrowing of blood vessels to internal organs and muscles. Patients with peripheral vascular disease are four times more likely to have a myocardial infarction and three times more likely to have a stroke. The five year mortality rate for people with peripheral vascular disease is 30 percent. Peripheral vascular disease affects 20 percent of the elderly and 40 percent of diabetics.

Unfortunately, it has been estimated that 8-12 million people in the United States are affected with this disease and the numbers are growing at a rate of five percent a year. Although these numbers show that peripheral vascular disease is a fairly common disease, peripheral vascular disease is often not diagnosed or is misdiagnosed. It has been estimated that 71 percent of physicians overlook a peripheral vascular disease condition in their patients.

It would be beneficial to have innovative techniques for diagnosing peripheral vascular disease. Additionally, it would be beneficial to have techniques of diagnosing peripheral vascular disease with relatively high accuracy rates.

BRIEF SUMMARY OF THE INVENTION

The present invention provides innovative techniques for diagnosing hypoxia conditions. Hypoxia is diagnosed through measurements of oxygen saturation. Some examples of hypoxia conditions that may be diagnosed include peripheral vascular disease, multiple organ dysfunction syndrome, ischemia, hypotension, and arteriosclerosis. In a specific implementation, a hypoxia condition is diagnosed based on changes in oxygen saturation in tissue. Ischemia is induced, and then measurements of changes in oxygen saturation in tissue are made. Based on changes in oxygen saturation, a diagnosis is provided of whether a patient has or does not have a hypoxia condition.

A hypoxia condition can occur when a region of the body is deprived of oxygen content. As one of skill in the art would understand, hypoxia conditions include, for example, peripheral vascular disease (PVD), multiple organ dysfunction syndrome (MODS), ischemia, hypotension, and arteriosclerosis. Techniques of the invention may be incorporated in devices or systems of the invention. For example, a device of the invention may use a technique or any combination or techniques described and then display a diagnosis of a hypoxia condition (e.g., provide a visual indication on a screen of a positive or negative test result).

Generally, oxygen saturation in tissue of a patient is monitored as part of a postocclusive reactive hyperemic (PORH) test. For example, blood flow to a limb can be reduced or stopped by utilizing a pressure cuff. The oxygen saturation of the limb can be monitored before, during, or after ischemia. The changes in oxygen saturation observed during the monitoring are then used to diagnose whether the patient has a hypoxia condition. In this manner, not only can a hypoxia condition be readily diagnosed, but the accuracy of the diagnoses can be relatively high.

In an embodiment, the invention is a method of diagnosing a hypoxia condition including: measuring oxygen saturation in tissue of a patient; analyzing the oxygen saturation in the tissue; and diagnosing the patient as having a hypoxia condition according to changes in the oxygen saturation in the tissue. In some embodiments, the measurement is an absolute value of chromophores or the ratio of chromophore concentrations.

Measuring of the oxygen saturation may occur during induced ischemia. In particular, the measurement may occur during an accumulation phase of the induced ischemia, an ischemia phase of the induced ischemia, a recovery phase of the induced ischemia, or a hyperemia phase of the induced ischemia.

In an embodiment, the invention is a method of diagnosing a hypoxia condition including measuring the oxygen saturation using continuous wave spectroscopy. In an embodiment, the measurements are taken by irradiating a physiological medium with at least one wave source and detecting using one wave detector.

In an embodiment, there may be two or more wave detectors, where distances between each pair of the wave source and wave detector are the same or almost the same: a first distance between a first wave source and a first wave detector is equal to a second distance between a second wave source and a second wave detector. In an embodiment, these distances between sources and detectors are different: a distance between a first wave source and a first detector is different from a distance between a second wave source and a second detector In an embodiment, the wave source provides at least two electromagnetic waves having different wave characteristics. These waves may be generated during irradiation. In an embodiment, the wave detector detects electromagnetic radiation transmitted through this physiological medium (e.g., blood). Analyzing the oxygen saturation in the tissue may be based on an absolute value of chromophores or a ratio of chromophore concentrations.

In an embodiment, the invention is a method including: inducing ischemia in tissue of a patient; measuring oxygen saturation of the tissue of the patient during a phase of the ischemia; and diagnosing the patient as having a hypoxia condition based on changes in the oxygen saturation of the tissue during at least one phase of the ischemia. For example, there may be four phases of the induced ischemia, an accumulation phase, ischemia phase, recovery phase, and hyperemia phase. Diagnosis of hypoxia may be made based on monitored changes in oxygen saturation (e.g., within any phase).

In an embodiment, the invention is a system including: a probe having a first detector input; a computer, connected to process signals received via the first detector input, to determine changes in oxygen saturation in tissue of a patient and make a diagnosis of a hypoxia condition based on the oxygen saturation changes; and a display, connected to the computer, to provide a visual indication of a positive diagnosis of a hypoxia condition.

In various specific embodiments, a diagnosis of a hypoxia condition is positive when the computer determines a rate of change in the oxygen saturation crosses a threshold value. A diagnosis of a hypoxia condition is positive when a measured time for the oxygen saturation to cross a percentage value during a phase after induced ischemia exceeds a specific time value. A diagnosis of a hypoxia condition is positive when a measured time, from a starting time value to an ending time value, for the oxygen saturation to cross a percentage value exceeds a specific time value. The starting and ending times may be within the same phase after induced ischemia. The starting time may be within a first phase after induced ischemia and the ending time may be within a second phase, different from the first phase, after induced ischemia.

In various specific embodiments, the probe includes a second detector input and a source output, and a first distance between the first detector input and the source output is different from a second distance between the second detector input and the source output. The probe includes a second detector input, a first source output, and a second source output, and a first distance between the first detector input and the first source output is different from a second distance between the second detector input and the second source output. The probe includes a second detector input, a first source output, and a second source output, and a first distance between the first detector input and the first source output is substantially the same as a second distance between the second detector input and the second source output.

Other features and advantages of the invention will become readily apparent upon review of the following description in association with the accompanying drawings, where the same or similar structures are designated with the same reference numerals.

BRIEF DESCRIPTION OF THE DRAWINGS

FIG. 7 shows results of diagnoses of patients for peripheral vascular disease utilizing the rate of recovery of oxygen saturation.

FIG. 11 shows results of diagnoses of patients for peripheral vascular disease utilizing the time oxygen saturation to recover a specified percentage.

DETAILED DESCRIPTION OF THE INVENTION

In the description that follows, the present invention will be described in reference to embodiments that diagnose peripheral vascular disease utilizing changes in oxygen saturation in tissue during recovery from ischemia. However, embodiments of the invention are not limited to any particular environment, application, or implementation. For example, although different techniques of monitoring changes in oxygen saturation will be described, the invention is not limited to the specific embodiments described below. Therefore, the description of the embodiments that follows is for purposes of illustration and not limitation.

Figure 1:
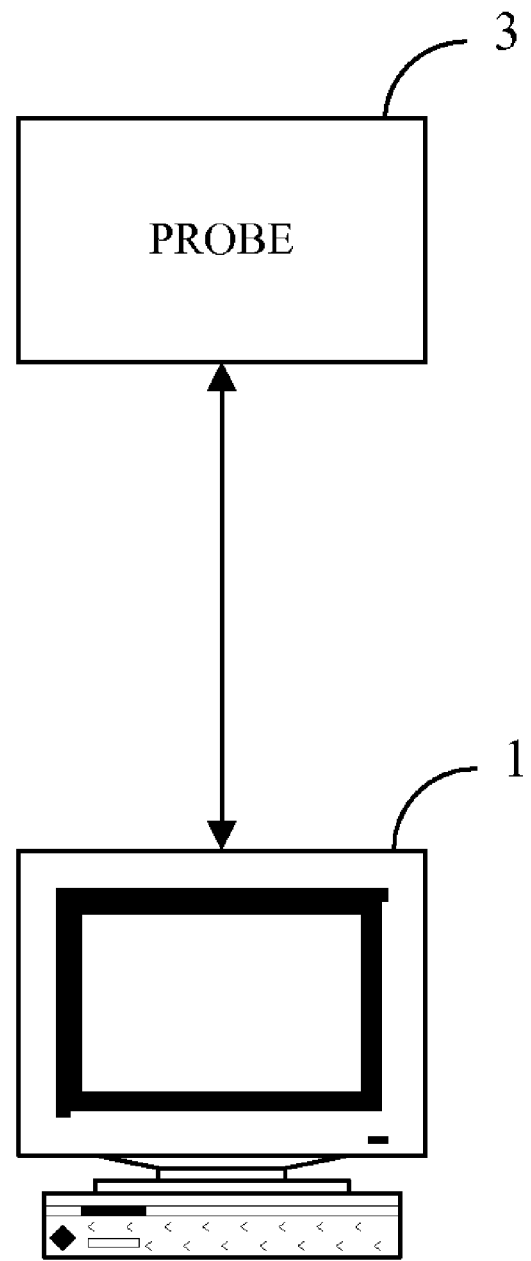
FIG. 1 shows an example of a computer system and probe for measuring oxygen saturation in tissue.

FIG. 1 shows an example of a system for diagnosing peripheral vascular disease. A computer system 1 is connected to a probe 3. Probe 3 is typically placed in close contact to a patient's tissue in order to collect data that can be analyzed by computer system 1 in order to determine oxygen saturation in the tissue.

In some embodiments, the system for measuring oxygen saturation in tissue is as described in U.S. patent application Ser. No. 09/877,515, filed Jun. 7, 2001, which issued as U.S. Pat. No. 6,587,703 on Jul. 1, 2003, which is incorporated by reference for all purposes. For example, the oxygen saturation system can use continuous wave spectroscopy (CWS) to determine absolute values of concentrations of oxygenated and deoxygenated hemoglobins in a patient's tissue. In other embodiments, other systems for measuring oxygen saturation in tissue can be utilized.

Figure 2:
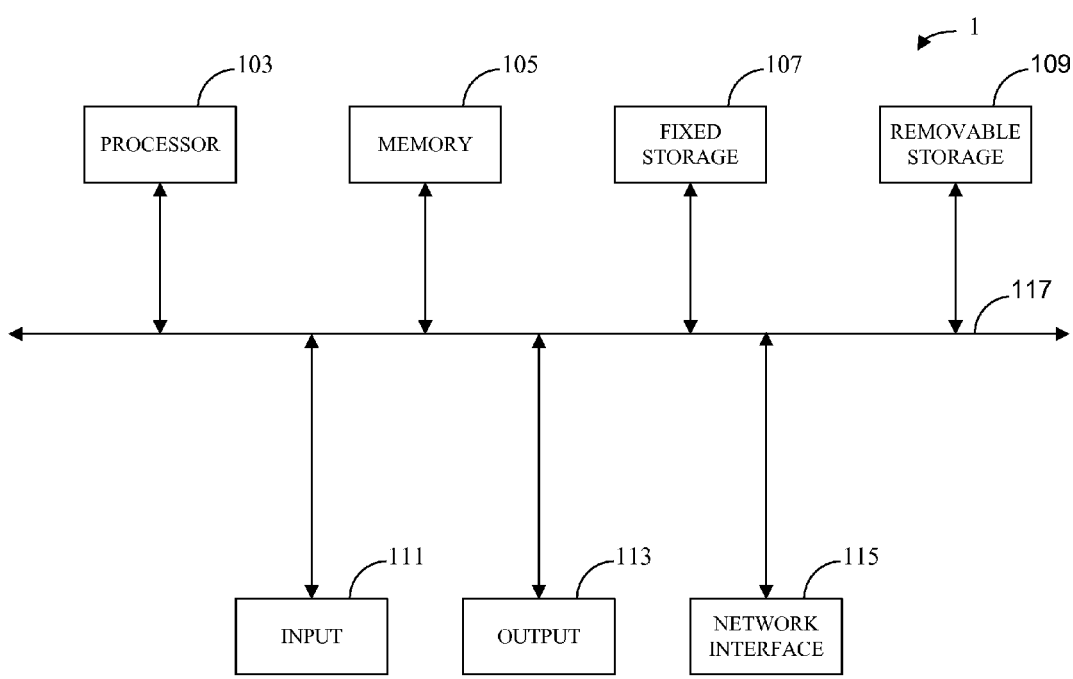
FIG. 2 illustrates a block diagram of a computer system that can be utilized in association with embodiments of the invention.

FIG. 2 shows a block diagram of components that can be present in computer systems that implement embodiments of the invention. A computer system 1 includes a processor 103 that executes instructions from computer programs (including operating systems). Although processors typically have memory caches also, processor 103 utilizes memory 105, which can store instructions or computer code and data.

A fixed storage (e.g., hard drives or drives) 107 can store computer programs and data such that it is typically persistent and provides more storage when compared to memory 105. A removable storage 109 provides mobility to computer programs and/or data that are stored thereon. Examples of removable storage are floppy disks, tape, CD-ROM, flash memory devices, and the like.

Memory 103, fixed storage 107, and removable storage 109 provide examples of computer readable storage media that can be utilized to store and retrieve computer programs incorporating computer codes that implement the invention, data for use with the invention, and the like. Additionally, a data signal embodied in a carrier wave (e.g., in a network including the Internet) can be the computer readable storage medium. An input 111 allows a user to interface with the system. Input can be done through the use of a keyboard, a mouse, buttons, dials, or any other input mechanism. An output 113 allows the system to provide output to the user. Output can be provided through a monitor, display screen, LEDs, printer, or any other output mechanism.

A network interface 115 allows the system to interface with a network to which it is connected. The system bus architecture of computer system 1 is represented by arrows 117. The components shown in FIG. 2 can be found in many computer systems. However, components can be added, deleted, and combined. Thus, FIG. 2 is for illustration purposes and not limitation.

Figure 3:
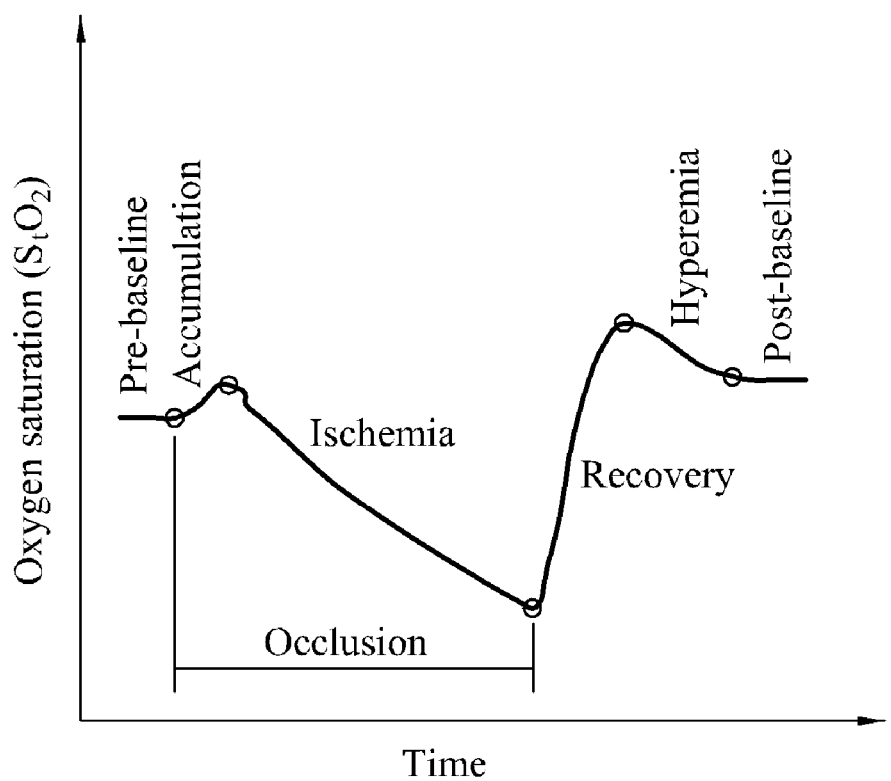
FIG. 3 shows a graph of oxygen saturation over time through induced ischemia and subsequent recovery.

FIG. 3 shows a graph of oxygen saturation through induced ischemia and subsequent recovery. The measurements were obtained as follows.

A subject was laying supine in a resting state. Sensors were positioned over the anterior tibialis muscle flat against the skin with minimal coupling pressure. Initial oxygen saturation measurements were then taken.

Occlusion of anterior blood flow to a lower limb was induced by inflating a cuff to 30 millimeter of mercury above systolic pressure. Cessation of blood flow was confirmed with a doppler. Occlusion was maintained for five minutes and then the occlusion was removed so that blood flow was rapidly restored. During this time, oxygen saturation was continuously monitored and recorded as indicated in the graph.

The graph in FIG. 3 can be broken into many different phases as shown. A prebaseline phase is where the cuff was not inflated and the subject was at rest. This stage shows the oxygen saturation level as a baseline before occlusion.

An accumulation phase is at the beginning of occlusion immediately following the cuff inflation, which causes oxyhemoglobin accumulation in the tissue.

An ischemic phase is the period following the accumulation phase while the cuff remained inflated and oxygen was being consumed. As shown, oxygen saturation steadily declines during this phase.

A recovery phase is the beginning post occlusive period, immediately following the cuff deflation, while fresh arterial blood is returning and oxygen saturation increases rapidly. As shown, oxygen saturation rose higher than the pre baseline oxygen saturation (called "overshooting").

A hyperemia phase was the last phase of a post occlusive reactive hyperemic (PORH) test. In the hyperemia phase, oxygen saturation decreased from its peak due to overshooting and reached the post occlusive baseline phase.

Figure 4:
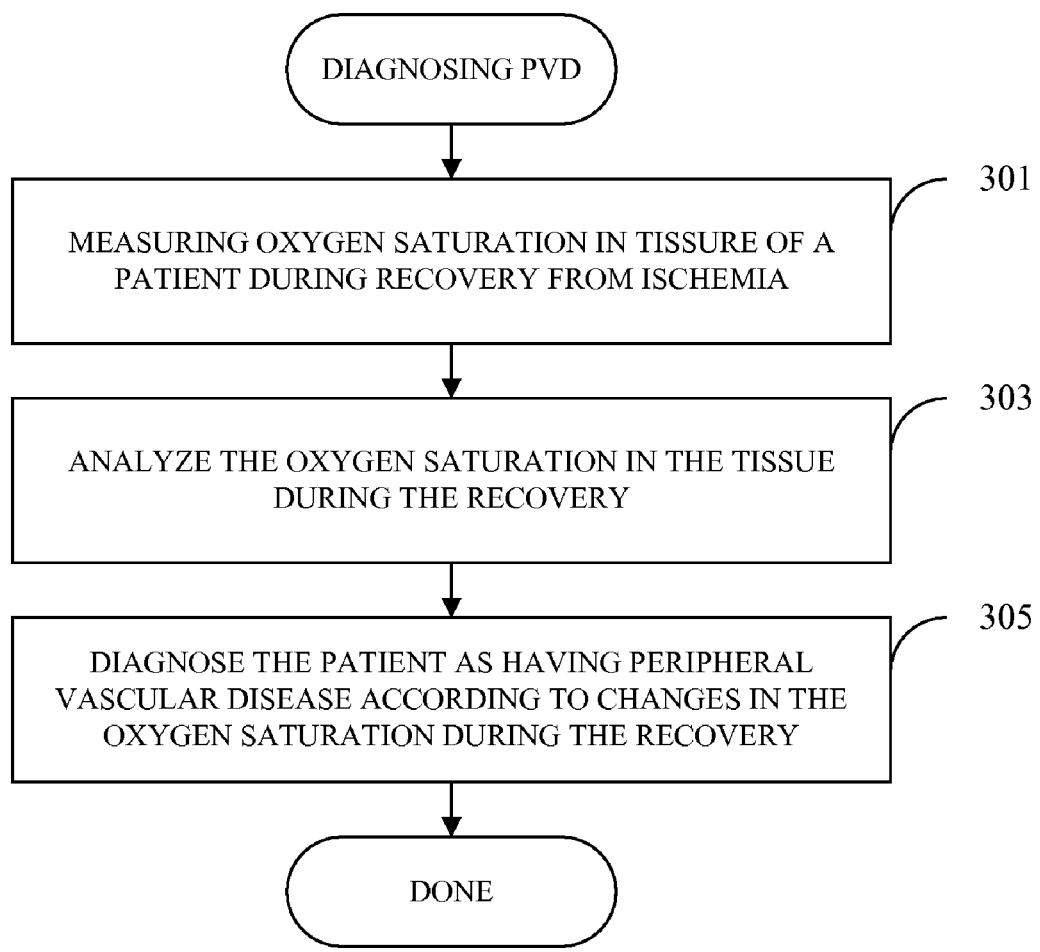
FIG. 4 shows a flow chart of a process of diagnosing peripheral vascular disease according to one embodiment of the invention.

Embodiments of the invention utilize changes in oxygen saturation during recovery from induced ischemia to diagnose peripheral vascular disease. FIG. 4 shows a flowchart of a process of diagnosing peripheral vascular disease utilizing changes in oxygen saturation during the recovery.

At a step 301, oxygen saturation in tissue of a patient during recovery from ischemia is measured. The oxygen saturation in the tissue during the recovery is analyzed at a step 303.

At a step 305, the patient is diagnosed as having peripheral vascular disease according to changes in the oxygen saturation during the recovery. The changes in oxygen saturation can be measured in various ways.

Figure 5:
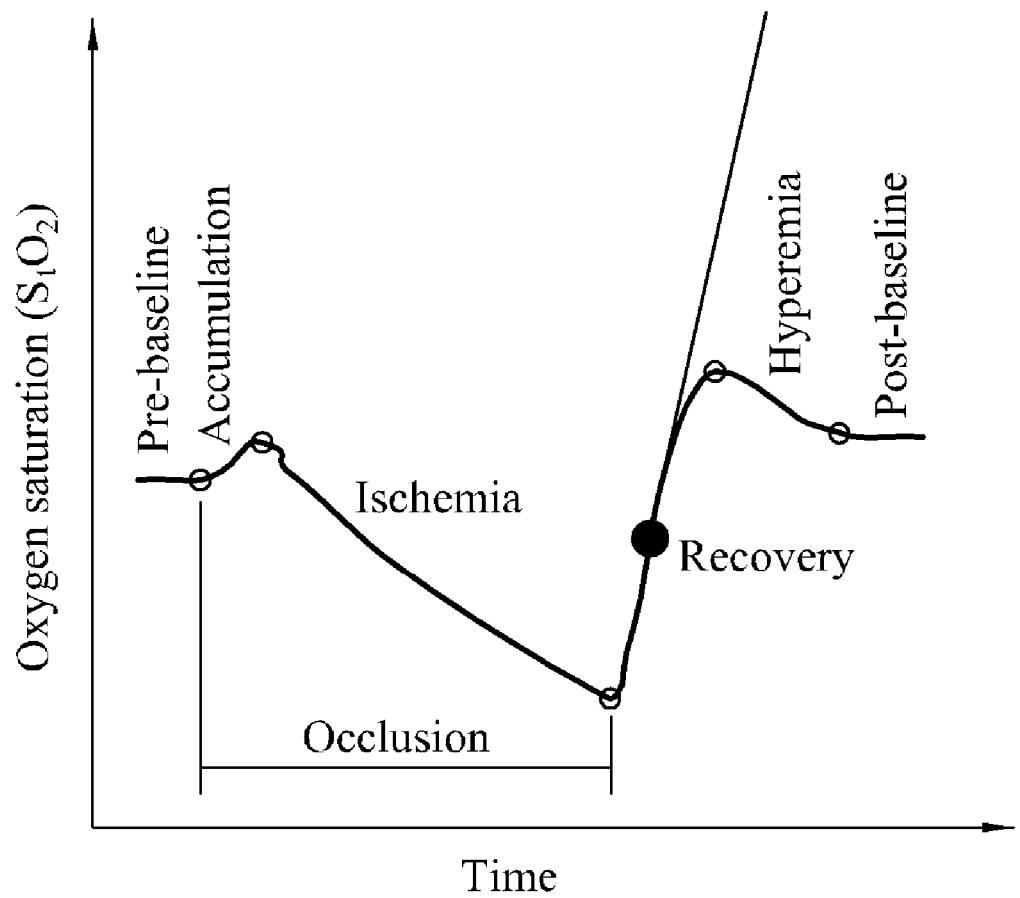
FIG. 5 shows a graph including the rate of change of oxygen saturation during recovery from ischemia.

In one embodiment, the changes in oxygen saturation are measured by the rate of change of oxygen saturation during recovery from ischemia. FIG. 5 shows a graph of the rate of recovery of oxygen saturation during recovery. As shown, the rate of change is measured at a midpoint in the recovery phase.

Figure 6:
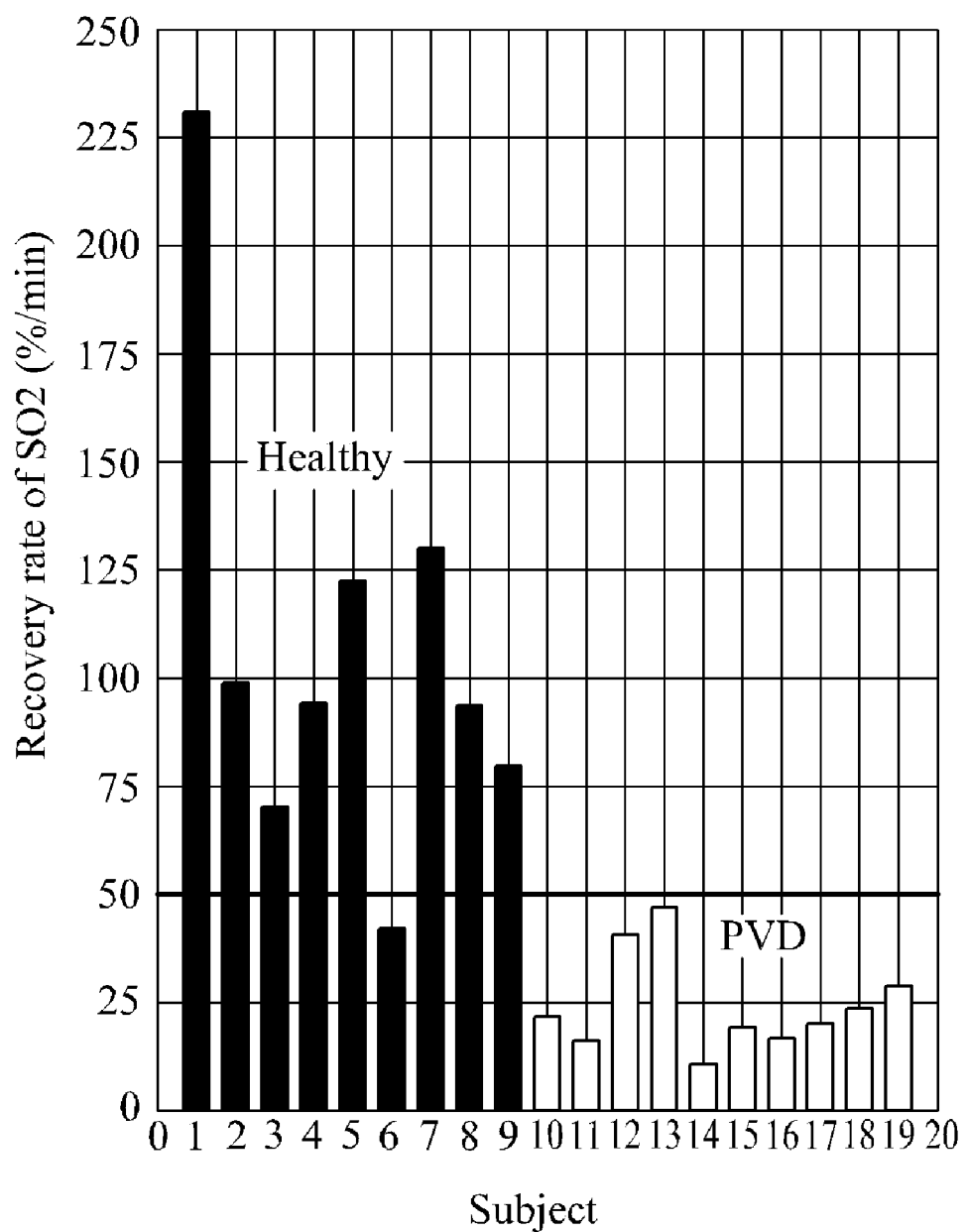
FIG. 6 shows a bar graph of various patients and diagnoses of peripheral vascular disease utilizing the rate of recovery of oxygen saturation.

FIG. 6 shows a bar graph of the rate of change of oxygen saturation during recovery for various patients. As shown, healthy patients have typically a higher rate of change of oxygen saturation during recovery. Accordingly a diagnosis of peripheral vascular disease can be made based on whether the rate of change oxygen saturation crosses a threshold (in this case is below a threshold), such as is shown in FIG. 6.

FIG. 7 shows results utilizing this technique for diagnosing peripheral vascular disease. As shown, there were ten true positives, eight true negatives, no false negatives and only one false positive.

Figure 8:
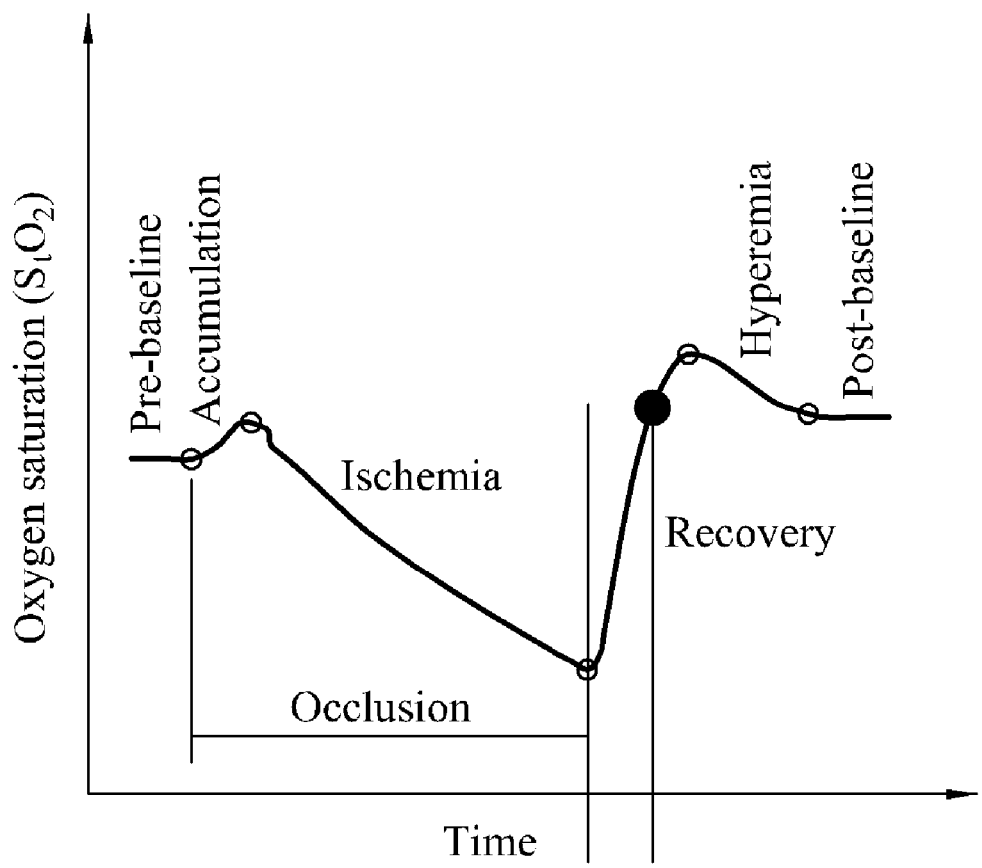
FIG. 8 shows a graph including the time for oxygen saturation to recover to a specified percentage during recovery from ischemia.

In another embodiment, the change in oxygen saturation during recovery is measured by the time for oxygen saturation to recover a specified percentage. FIG. 8 shows a graph of the time needed for oxygen saturation to recover 80 percent of the oxygen saturation through the recovery phase.

Figure 9:
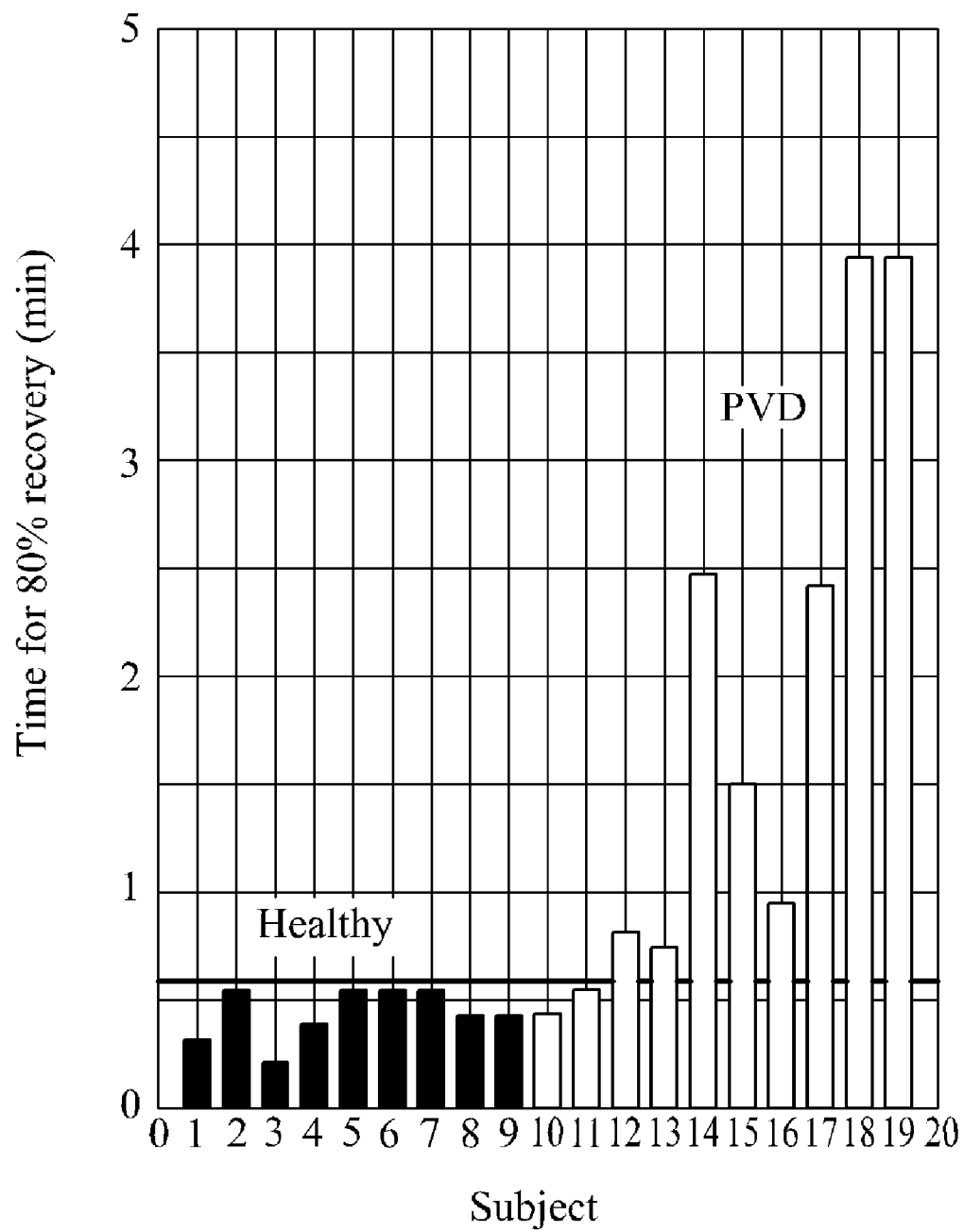
FIG. 9 shows a bar graph of various patients and the diagnoses of peripheral vascular disease utilizing the time for oxygen saturation to recover a specified percentage.

FIG. 9 shows a bar graph of the time for oxygen saturation to recover to a specified percentage during recovery for various individuals. As shown, patients with peripheral vascular disease demonstrated more time was taken to recover oxygen saturation to 80 percent. Accordingly, peripheral vascular disease can be diagnosed according to whether the time for oxygen saturation to recover a specified percentage crosses a threshold (in this case is above a threshold) as shown in FIG. 9.

Figure 10:
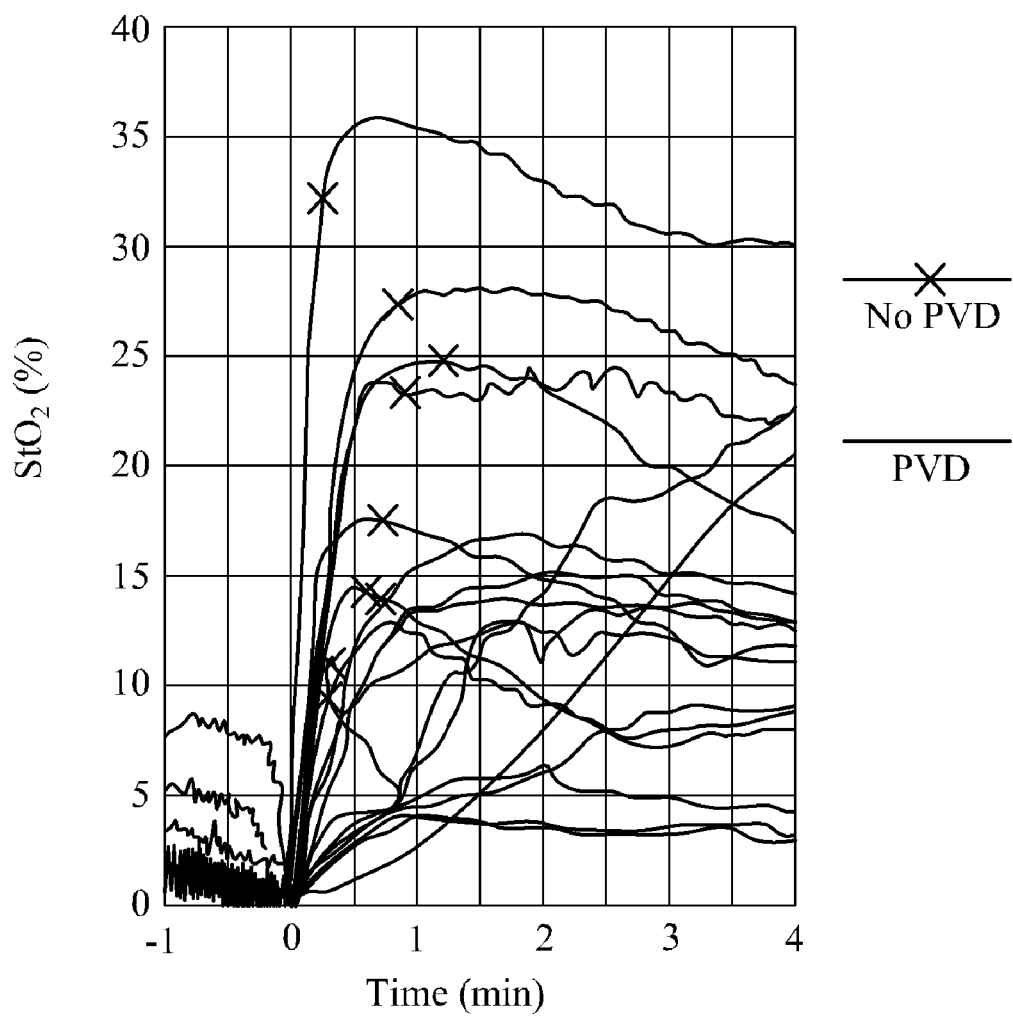
FIG. 10 shows a graph of patients and their oxygen saturation recovery over time.

FIG. 10 shows a graph of the oxygen saturation in tissue of patients over time for patients without peripheral vascular disease and with peripheral vascular disease. As shown, patients without peripheral vascular disease typically recover oxygen saturation more quickly than patients with peripheral vascular disease.

FIG. 11 shows results from varies patients utilizing this technique for diagnosing peripheral vascular disease. As shown, there were eight true positives, nine true negative, zero false positives and only two false negatives.

Although the preceding has described different methods for measuring changes in oxygen saturation during recovery, the invention can utilize any methods of measuring any changes oxygen saturation. Additionally, one or more different methods of measuring changes in oxygen saturation during recovery can be combined in order to provide diagnoses for peripheral vascular disease.

Figure 12:
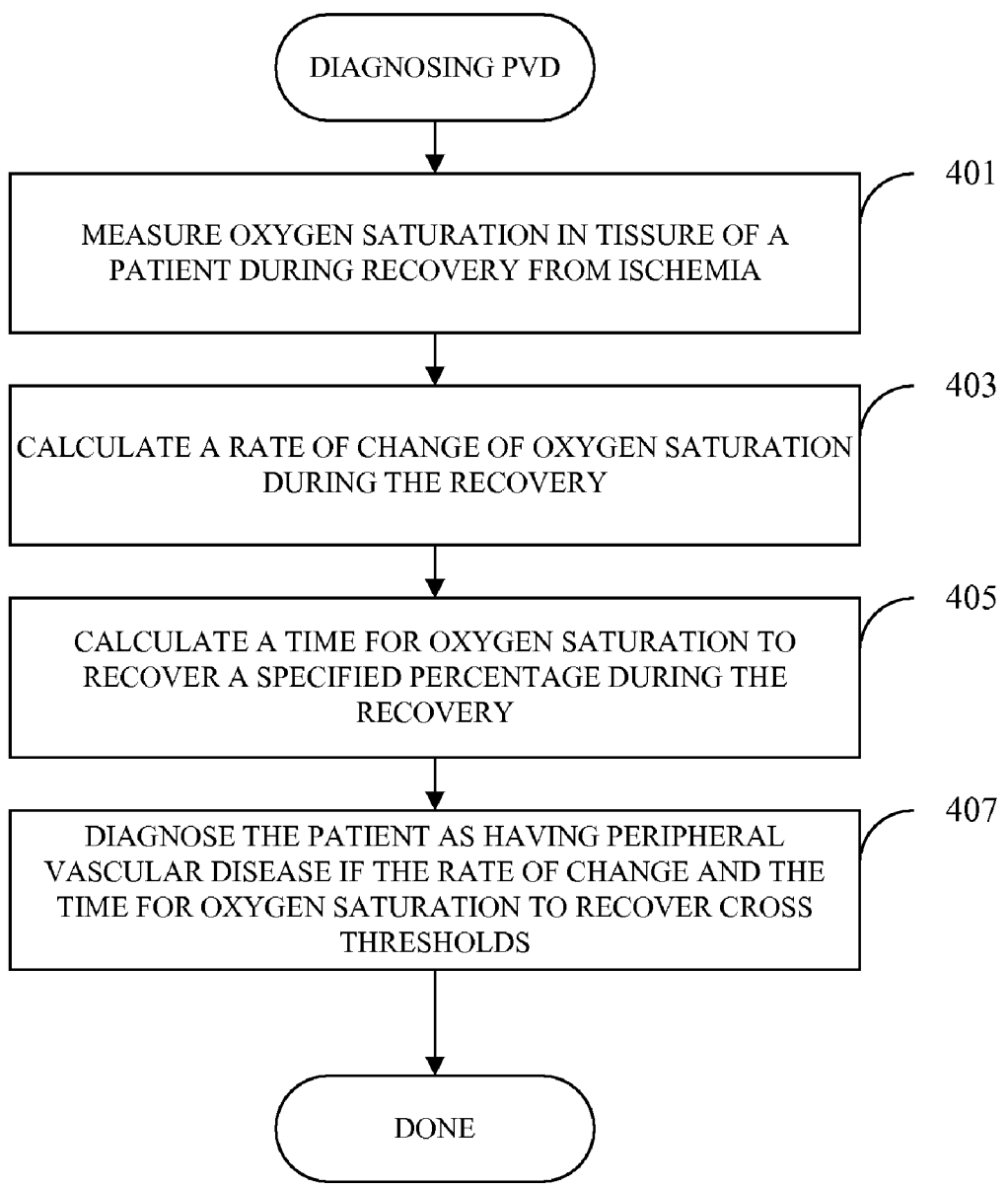
FIG. 12 shows a flow chart of another process of diagnosing peripheral vascular disease according to the invention.

FIG. 12 shows a flow chart of another process of diagnosing peripheral vascular disease. At a step 401, oxygen saturation in tissue of a patient during recovery from ischemia is measured. A rate of change of oxygen saturation during the recovery is calculated at a step 403. The rate of change can be calculated as described previously. At a step 405, a time for oxygen saturation to recover a specified percentage during the recovery is calculated. The time can be calculated as discussed previously.

At a step 407, the patient can be diagnosed as having peripheral vascular disease if the rate of change and the time for oxygen saturation to recover cross thresholds. By utilizing multiple methods of measuring changes in oxygen saturation during recovery, greater accuracy in diagnosing peripheral vascular disease can be obtained.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method of diagnosing a peripheral vascular disease condition comprising:
   measuring oxygen saturation in tissue of a patient;
   analyzing the oxygen saturation in the tissue; and
   determining a rate of change of the oxygen saturation in the tissue
   using at least one processor, diagnosing the patient as having the peripheral vascular disease condition based on the rate of change of the oxygen saturation crossing a value in the tissue.

2. The method of claim 1 wherein the peripheral vascular disease condition comprises multiple organ dysfunction syndrome.

3. The method of claim 1 wherein the measuring of the oxygen saturation occurs during induced ischemia.

4. The method of claim 3 wherein the measuring of the oxygen saturation occurs during a recovery phase of the induced ischemia.

5. The method of claim 4 wherein during the recovery phase, the rate of change is a positive number when the oxygen saturation in the tissue increases over time.

6. The method of claim 3 wherein during induced ischemia, the rate of change is a negative number when the oxygen saturation in the tissue falls over time, and after the induced ischemia, the rate of change becomes a positive number when the oxygen saturation in the tissue increases over time.

7. The method of claim 1 wherein the measuring of the oxygen saturation is determined using continuous wave spectroscopy.

8. The method of claim 1 wherein the measuring of the oxygen saturation is determined by irradiating a physiological medium with at least one wave source and detecting using at least one wave detector.

9. The method of claim 8 wherein during the irradiating, the at least one wave source outputs at least two electromagnetic waves having different wave characteristics.

10. The method of claim 8 wherein during the detecting, the at least one wave detector receives electromagnetic radiation transmitted through a physiological medium.

11. The method of claim 8 wherein a first distance between a first wave source and a first wave detector is equal to a second distance between a second wave source and a second wave detector.

12. The method of claim 1 wherein the analyzing the oxygen saturation in the tissue is based on an absolute value of chromophores.

13. The method of claim 1 wherein the analyzing the oxygen saturation in the tissue is based on a ratio of chromophore concentrations.

14. The method of claim 1 wherein the rate of change of the oxygen saturation in the tissue is measured at a single tissue site.

15. The method of claim 1 wherein the diagnosing the patient as having the peripheral vascular disease condition based on the rate of change of the oxygen saturation in the tissue comprises:
making a positive diagnosis of a peripheral vascular condition when the rate of change in the oxygen saturation crosses a threshold value.

16. A method comprising:
measuring oxygen saturation of the tissue of the patient;
determining a rate of change of the oxygen saturation in the tissue; and
using at least one processor, diagnosing the patient as having a peripheral vascular disease condition based on the rate of change of the oxygen saturation crossing a value in the tissue during at least one phase of ischemia.

17. The method of claim 16 comprising:
inducing ischemia in tissue of a patient.

18. The method of claim 17 wherein the measuring of the oxygen saturation occurs during a recovery phase of induced ischemia.

19. The method of claim 18 wherein during the recovery phase, the rate of change is a positive number when the oxygen saturation in the tissue increases over time.

20. The method of claim 18 wherein during induced ischemia, the rate of change is a negative number when the oxygen saturation in the tissue falls over time, and after the induced ischemia, the rate of change becomes a positive number when the oxygen saturation in the tissue increases over time.

21. A system comprising:
a probe comprising a first detector input;
a computer, coupled to process signals received via the first detector input, to determine a rate of change of oxygen saturation crossing a value in tissue of a patient and make a diagnosis of a peripheral vascular disease based on the rate of change crossing a value; and
a display, coupled to the computer, to provide a visual indication of a positive diagnosis of peripheral vascular disease.

22. The system of claim 21 wherein the diagnosis of a peripheral vascular disease is positive when the computer determines the rate of change in the oxygen saturation crosses a threshold value.

23. The system of claim 22 wherein the threshold value is a rate of change in oxygen saturation in the tissue.

24. The system of claim 22 wherein when the rate of change crosses the threshold value, the patient has the peripheral vascular disease condition.

25. The system of claim 21 wherein the probe comprises a second detector input, a first source output, and a second source output, and a first distance between the first detector input and the first source output is substantially the same as a second distance between the second detector input and the second source output.

26. The system of claim 22 wherein the rate of change in the oxygen saturation is measured during induced ischemia of the tissue.

27. The system of claim 22 wherein the rate of change in the oxygen saturation is measured during a recovery phase of induced ischemia of the tissue, wherein the rate of change is a positive number.

28. The system of claim 27 wherein the rate of change is measured at a midpoint in the recovery phase, when the oxygen saturation in the tissue is halfway between a lowest value of oxygen saturation during induced ischemia and a baseline value before the induced ischemia.

29. The system of claim 27 wherein the rate of change is inversely related to a likelihood of a positive diagnosis of a hypoxia condition.

30. The system of claim 26 wherein the rate of change in the oxygen saturation rises above the threshold value.

31. The system of claim 21 comprising measuring the oxygen saturation in tissue during a recovery phase of induced ischemia, and the rate of change is a positive number when the oxygen saturation in the tissue increases over time during the recovery phase.

32. The method of claim 31 wherein during induced ischemia, the rate of change is a negative number when the oxygen saturation in the tissue falls over time, and after the induced ischemia, the rate of change becomes a positive number when the oxygen saturation in the tissue increases over time.

* * * * *